United States Patent [19]

Wiesenberger et al.

[11] Patent Number: 4,702,922

[45] Date of Patent: Oct. 27, 1987

[54] FRUIT PRODUCTS CONTAINING LACTIC ACID AND PROCESS FOR THE LACTIC ACID FERMENTATION OF FRUIT PRODUCTS

[75] Inventors: Alfred Wiesenberger, Wiesbaden-Sonnenberg; Jens A. Schildmann, Partenheim; Erich Kolb, Nieder-Olm; Hans-Mario Dechent, Saulheim, all of Fed. Rep. of Germany

[73] Assignee: Peter Eckes KG mbH, Nieder-Olm, Fed. Rep. of Germany

[21] Appl. No.: 826,515

[22] Filed: Feb. 5, 1986

[30] Foreign Application Priority Data

Feb. 5, 1985 [DE] Fed. Rep. of Germany ....... 3503742

[51] Int. Cl.$^4$ .......................... A23L 1/212; A23L 1/06

[52] U.S. Cl. ........................................ 426/51; 426/52; 426/599

[58] Field of Search ............................ 426/51, 52, 599

[56] References Cited

U.S. PATENT DOCUMENTS 2,982,657  5/1961  Keitel .................................... 426/51
3,420,672  1/1969  Keitel .................................... 426/51

Primary Examiner—Raymond N. Jones
Assistant Examiner—Marianne M. Cintins
Attorney, Agent, or Firm—Beveridge, DeGrandi & Weilacher

[57] ABSTRACT

A process for the lactic acid fermentation of fruit products is disclosed wherein an initial product in the form of a mash or juice having a pH of less than 3.7 is pasteurized and thereafter subjected to fermentation by lactic acid producing bacteria which produce at least 95% L(+) lactic acid as the fermentation product.

17 Claims, 3 Drawing Figures

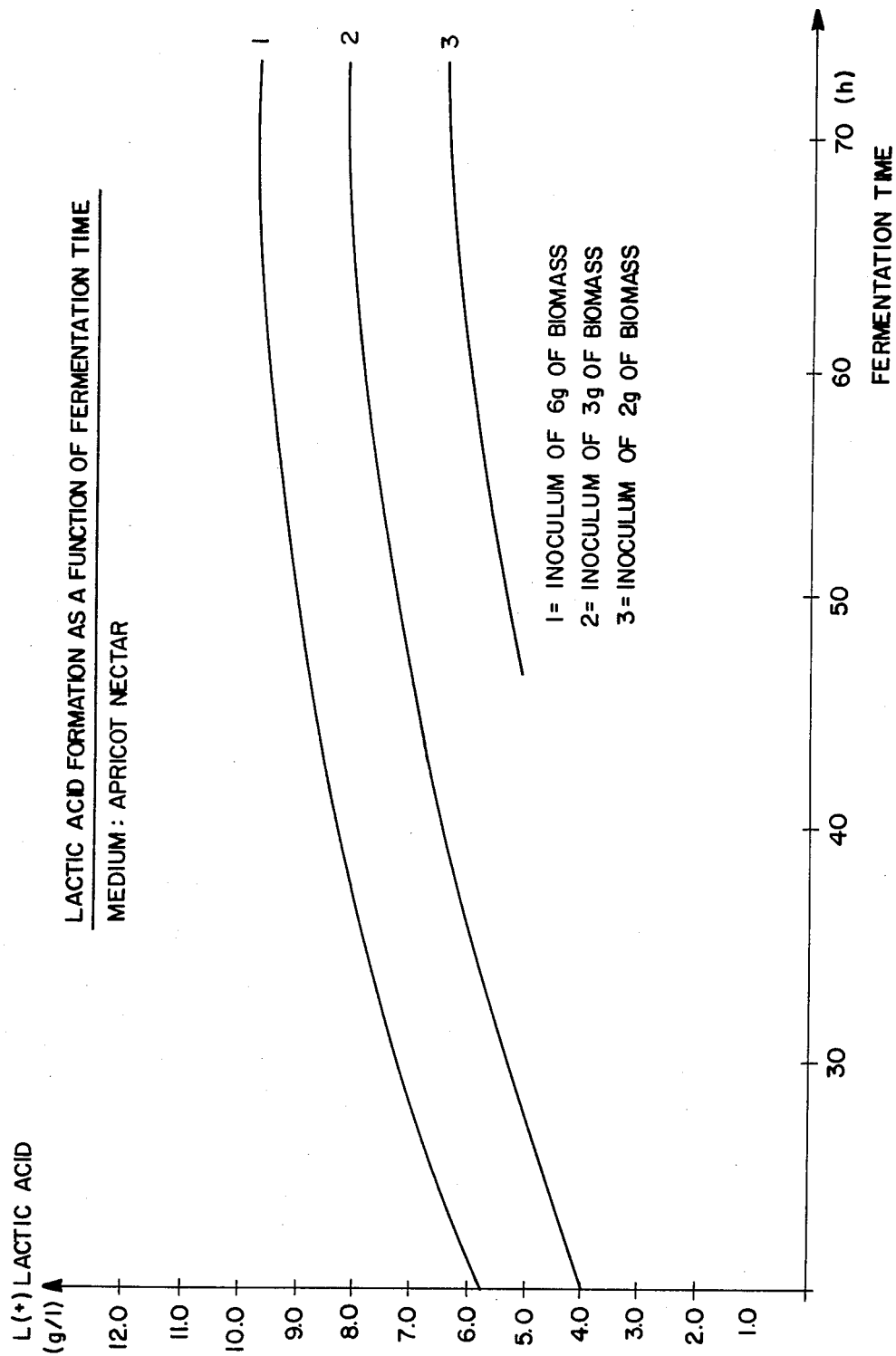

FRUIT PRODUCTS CONTAINING LACTIC ACID AND PROCESS FOR THE LACTIC ACID FERMENTATION OF FRUIT PRODUCTS

The invention relates to a process for the lactic acid fermentation of fruit products, in which the initial product in the form of a mash or juice, after destruction of the wild microflora therein, is subjected to fermentation by lactic acid producing bacteria, which produce at least 95% L(+) lactic acid as the fermentation product.

The method of the present invention can advantageously utilize juices derived from fruits as starting materials as well as other starting materials obtained from fruit, which exhibit a pH value of less than 3.7.

Among suitable fruits that can be used according to the present invention are well known fruits which have a relatively acidic taste such as apples, white and red wine grapes, apricots, sour cherries, peaches, pears, oranges, black and red currants and the like.

According to the present invention, starting materials such as juices, nectars, mashes, pulps or other mixtures are produced from such fruits. Juices include clear as well as cloudy juices which are obtained by pressing or squeezing these fruits.

As used herein, the term "nectar" which has a recognized meaning under the food laws of some countries, is understood to include fruit nectar or fruit syrup; that is, unfermented but capable of fermentation through the addition of water and/or sugar to optionally concentrated fruit juices or optionally concentrated fruit pulp or a mixture of such products, whereby these produced substances corresponding to the indicated criteria are defined by a minimum fruit content and a minimum acid content. Accordingly, a nectar obtained from black or red currants should have a fruit content of at least 25 weight percent and an acid content of at least 8 parts per 1000 (calculated as tartaric acid), that is 8 g/l of nectar. Similarly, a sour cherry nectar should contain at least 35 weight percent fruit content and 8 parts per 1000 of acid; apricot nectar should contain at least 40 weight percent of fruit content and at least 6 parts per 1000 of acid; and a peach nectar should contain at least 45 fruit content by weight and at least 3 parts per 1000 of acid.

The carrying out of the process of the invention is, of course, not limited to the utilization of such nectars. Thus, the process of the present invention as described herein is also suitable for nectars which have other characteristics such as a higher or lower fruit and/or acid content.

As has been mentioned, the method of the present invention can also utilize as the starting material a fruit pulp. In this application, the expression "pulp" is intended to include the edible portion of peeled and cored fruit which, through a variety of different processing steps have been converted into a pulp.

Within the context of the invention, fruit products are understood to include fruit juices, fruit juice mixtures, fruit pulp, fruit pulp mixtures, and mixtures of the above mentioned four components, which may also contain admixtures of water, sugar, honey, etc. The scope of the meaning of "fruit products" also includes jams, preserves, fruit bars, jellies, spreads and the like in which the basic component is a fruit pulp.

Lactic acid producing fermentations have long been known in the art. As a single example thereof the preparation of sauerkraut can be mentioned. In the past, lactic acid fermentation was mainly used to render certain moist articles of consumption less perishable. Later on, the object of lactic acid fermentation was also to improve the nutritive values and sensory properties of largely vegetable mashes and juices by a better digestion of the foodstuff and by the resulting acids. In many cases, however, undesirable by-products that call into question the sensory gains sought through fermentation also arise in conventional heterofermentative lactic acid fermentation.

In recent times, an ever increasing importance has been attached not only to an acidulation of the product by the production of lactic acid as such during the lactic acid fermentation, regardless of whether the acid is levo- or dextrorotatory, but rather to the formation of the physiologically active L(+) lactic acid. To this end, special homofermentative bacterial cultures were selected that are capable of producing essentially L(+) lactic acid.

The presence of L(+) lactic acid in almost all organs and tissues in the human body substantiates its importance for cell reactions. The higher the energy output of an organ, the greater the L(+) lactic acid requirement. Therefore, a balanced metabolism always requires a potential of L(+) lactic acid, which maintains the functions of the organs and tissues, especially of muscles, liver, and heart. The supply of L(+) lactic acid in the typical daily diet is generally below metabolic requirements of this substance, so it is desirable to enrich these foods with L(+) lactic acid from which L(+) lactic acid is immediately available for metabolism.

A process suggesting this direction is described in German Pat. No. 2 001 874, which has as its object the preparation of lactic acid vegetable or fruit juices. In this patent, four special bacterial strains are described, including *Lactobacillus casei*, which are used to ferment vegetable or fruit mashes or juices after destruction of the wild lactic acid producing bacteria found therein, a process during which lactic acid is produced, at least 90% of which consists of L(+) lactic acid. Examples given in this prior publication are the fermentation of carrot mash, carrot juice, red beet juice, and banana mash. Without exception, these mashes and juices are products with a very low initial acid content, i.e., a pH between approximately 5.0 and 6.0. The fermentation is carried out specifically to acidulate the products and, according to the details given in the above patent, it reaches a final pH of approximately 3.7 to 3.9 after a fermentation time of 12 to 20 hours. According to the tables following the specific examples, even somewhat lower pH values were obtained after a fermentation time of 24 hours with certain mixtures of bacterial cultures indicated therein. However, these examples also suggest that the ratio of L(+) lactic acid to D(−) lactic acid shifts considerably with increasing fermentation time and lower pH values, so that in one case a content of up to 90%, while in other cases only 50% to 60%, L(+) lactic acid is obtained.

Another feature of the process known from the prior art is that microbial growth occurs in the product being fermented. Admittedly, the microorganisms, which are then used to inoculate the main batch, are previously enriched in smaller amounts of the same product, but this amount of inoculant is basically just large enough to initiate further growth of the microorganisms in the main batch; the fermentation thus proceeds with a very active microbial growth. In this process, growth by-products may appear, which, under certain circumstances, are detrimental to a perfect sensory result.

Another bacterial strain, *Lactobacillus bavaricous*, for the lactic acid fermentation of plant materials is described in German Pat. No. 24 40 516. The specific examples described therein are concerned with the preparation of sauerkraut and pickles. The pH after 20 days is 3.9 to 3.8.

The present invention has as its object the provision of a process for the lactic acid fermentation of fruit products, which enables the production of appreciable amounts almost exclusively of the physiologically active L(+) lactic acid in fruit products, whose initial acidity is already relatively high, by fermentation without deleteriously affecting the sensory qualities of the products, but rather improving them as much as possible. In this process, the question is not to achieve a certain acidulation of a slightly sour initial product for sensory reasons, as is the case in conventional processes, but rather to convert a portion of the substances in the naturally already rather sour initial fruit into L(+) lactic acid without appreciable growth of the bacteria during further degradation of the sugar ingredients in the juice.

It has now been unexpectedly found that the starting fruit products that exhibit an initial pH value of 3.7, or even preferably 3.2 to 3.6, can be treated with lactic acid producing bacteria. Under these conditions, it has been found that in a large predominant amount, the malic acid content of such fruit products is converted into lactic acid.

According to the invention, the aforementioned object is achieved by employing bacteria whose lactic acid producing metabolic pathways are induced and which function even at pH values below 3.7, and by carrying out the fermentation at pH values below 3.7, during which process a portion of L(+) lactic acid of at least 95 weight percent is produced. Generally, a pH of a minimum of 3 is necessary in order to avoid adversely affecting the microorganism. Advantageously, the starting fruit products exhibit a pH in the range of 3.2 to 3.6.

It has been shown that during lactic acid fermentation at pH values below 3.7 certain sugars are not only fermented to lactic acid, but a portion of the organo acids, especially malic acid, found in the initial products, are also converted to lactic acid by the bacterial strains used. A sensory gain is thereby achieved to a certain extent, because the malic acid with its more acidic taste is replaced by the milder lactic acid with its more pleasant sensory effects. Therefore, the fermentation product in general does not exhibit any detectable malic acid content with any certainty, advantageously it contains a malic acid content of not more than 0.1 g/l, particularly not more than 0.2 to 0.5 g/l. With undiluted starting fruit products, according to circumstances, a malic acid content can achieve a maximum of 1 g/l. A corresponding higher value can naturally arise with further processing of the fermentation product to produce an end product, when the fermentation product is concentrated or is mixed with an unfermented starting material.

For undiluted fruit mass (juice or pulp), the following indicated content values for malic acid content are indicated: oranges 1-2 g/l, apples 4-5 g/l, grapes 4-5 g/l, peaches over 2 g/l, aprictts 4-5 g/l and sour cherry juice 17 g/l. With these starting substances, a wide ranging elimination of the malic acid content takes place. As an exception, the juice and nectar of black currants exhibit a very low content of malic acid. The acidulation of quite a few citric acid containing products, such as peach pulp, is also desirable, during which process the L(+) lactic acid is synthesized from sugar.

Preferably, the fermentation process is carried out in such a way that at least 5 g, preferably 6 g/l, of L(+) lactic acid is produced per liter of fermentation product. It is possible, however, to attain higher lactic acid levels depending on the raw material and process conditions. If these higher lactic acid levels are not required, the fermentation product can later be adjusted to a content of 5 g per liter with the unfermented product.

As described in accordance with the process herein, the pH value of the obtained product is maintained under a pH of 3.7, preferably in a range of 3.0 to 3.6, especially 3.1 to 3.4. Conversion of the malic acid, which is a weaker acid than the lactic acid, causes the resulting product to regularly exhibit a somewhat higher acidity than the starting material; that is, the pH value of the resulting product is usually somewhat lower than the pH value of the starting substance. For the reason that, as a general rule, the naturally occurring juices exhibit a high buffering capacity, the final pH value can correspond to the pH value of the starting substances. During the fermentation, the pH value can even rise by about 0.1, whereby it can be determined that according to the invention, the starting pH value is regularly from 0.1 to 0.2 points higher than the pH value at the end, as has been previously explained.

A particularly preferred embodiment of the process of the present invention resides in the addition of the bacteria; i.e., the biomass, as a pure culture concentrate to the initial product to be fermented. The snowball system of microbial enrichment in the product to be fermented is undesirable due to its sensorially negative effects particularly in fruit juice products. Therefore, according to the invention, amounts that are appropriate for the fermentation of the selected microorganisms are added to maintain the target amount of L(+) lactic acid as a metabolite of the organisms.

In the final analysis, no microbial growth occurs in the process taught by the present invention. On the contrary, the death rate lies in the 50% range. When the fermentation is completed, about ⅓ to ⅔ of the initially added amount of living biomass is still present in the product.

In a preferred embodiment of the the present invention process, the remaining biomass is removed from the product at the end, because the fermentation products so obtained are the actual goal sought by the process of the invention. This removal of the biomass is especially desirable during the preparation of clear fruit juice products. On the other hand, it is not detrimental to the process results if, dependent upon the type of desired end product, the residual amount of biomass remaining after fermentation is left in the product.

The bacterial strains are cultured in a separate, known fermentation process under optimum nutrient and growth conditions, as will be described in greater detail hereinbelow.

Accordingly, at least 1 g, but usually 2 to 10 g, of moist purified biomass is to be added per liter of the initial product to be fermented. For reasons of economy, the added amount will essentially vary from 2 to 6 g. The amounts indicated herein refer to a purified bacterial mass of 21-25%, generally about 23%, solids. The bacterial count is about $10^{12}$ per gram of this biomass.

The duration of the fermentation time for the process being described is generally at least 24 hours, but this can be increased to 96 to 100 hours in special cases. The optimum fermentation time is determined by economic considerations with respect to the biomass added and the fermentation temperature selected. The latter can range from 15° to 40° C.; with temperatures between 25° C. and 35° C. being preferred. However, in the case of particularly sensitive products, it may be desirable for the fermentation to proceed at a temperature below 20° C., for which reason the bacterial strains employed are also suitable for this purpose.

Several suitable bacterial strains were selected or isolated for the process described herein. A microorganism of the genus Lactobacillus isolated in this regard and suitable for carrying out the process was given the designation Lactobacillus sp. In the research carried out, this strain was identified as Beta 8. Cultures of this organism were filed under the deposit No. DSM 3174 in the German Collection of Microorganisms (DSM) in Goettingen. This microorganism was selected from orange juice, then initially cultured on Rogosa agar and transferred to MRS broth (obtained from the OXOID company under the article number CM 359).

These are motile lactobacilli with mesodiaminopimelic acid in their cell wall. The strains differ from the known Lactobacillus species with these characteristics (*L. aqilis, L. yamanashiensis and L. ruminis*) in a number of characteristics such as growth temperature, gluconate utilization and the base composition of the DNA, so that this is a representative of a species not previously described.

Lactobacillus sp. consists of gram positive rods and is nonsporing. It is catalase- and nitrate-reductase negative. It is a facultatively anaerobic strain. The microorganisms are homofermentative; glucose is fermented solely into lactic acid. The resulting synthesized lactic acid consists of 95 to 99% of the L(+) component.

Ribose, mannitol, sorbitol, maltose, sucrose, cellobiose, trehalose, salicin, and glucose are fermented into lactic acid by this Lactobacillus. No lactic acid is produced from arabinose, xylose, rhamnose, lactose, melibiose, raffinose, and melezitose. Growth of the new bacillus is positive at 15° C. and negative at 45° C. Gas evolution from gluconate is positive.

Lactobacillus sp. for carrying out the present invention is cultured in MRS broth. 1 g of biomass per liter of broth produces a 15-fold increase in the biomass after 24 hours at 33° C. A BETA nutrient solution is introduced aseptically into a commercially obtainable laboratory fermentor; the biomass yield relative to the nutrient solution is considerably increased by the concurrent addition of a pH-regulating solution (4M NaOH) and a glucose solution of defined concentration (40° Brix). The BETA nutrient solution employed has the following composition:

TABLE 1

Composition of the BETA Nutrient Solution
(amounts required for 1 liter of nutrient solution)

| Peptonized milk | 10.00 g |
|---|---|
| Yeast extract | 12.00 g |
| Dextrose | 20.00 g |
| Tween 80 (surfactant) | 1.00 g |
| Potassium phosphate | 2.00 g |
| Sodium acetate | 5.00 g |
| Diammonium hydrogen citrate | 2.00 g |
| Magnesium sulfate × 7H$_2$O | 0.20 g |
| Manganese sulfate × 4H$_2$O | 0.05 g |

The microorganisms are harvested and collected by a membrane separation procedure. The biomass thus obtained is purified with physiologic saline and added as a pure culture to the fruit products. Such separation and purification methods are well known and any suitable procedure may be used for purposes of this invention.

For the fermentation of fruit products, this biomass is added to, for example, apple juice, peach nectar, or cherry nectar. The process conditions are to be defined in detail for each individual product on the basis of sensory and economic interests within the limits indicated above.

It has been found that certain other bacterial strains are also suitable for the present process. Thus, for example, the microorganism *Lactobacillus casei subspecies casei* as filed under deposit No. DSM 3173 in the German Collection for Microorganisms (DSM) in Göttingen is also suitable. This strain was identified by the designation Beta 3 for this research.

These are gram-positive nonmotile rods, 0.8 to 2-3 μm in size, usually found in chains. They are nonsporing, facultative anaerobes, homofermentative, and inevitably saccharoclastic; the end product of glucose fermentation is strictly lactic acid L(+) lactic acid is produced almost exclusively.

The bacterium is catalase- and nitrate reductase-negative. Growth occurs between 15° C. and 45° C. Gluconate is utilized. Acid is produced from ribose, mannitol, sorbitol, glucose, maltose, lactose, sucrose, cellobiose, trehalose, and salicin. No acid is produced from arabinose, xylose, rhamnose, melibiose, and raffinose.

The peptidoglycan of the cell wall contains no diaminopimelic acid. Of the few selected strains, out of a total of over 100 tested types which are suitable for the above described process, the two strains described herein were found to exhibit particularly advantageous sensory properties.

Some typical process results are summarized in Table II, which contains a range of preferred products. For the experiments, both the Beta 8 and the Beta 3 strains were used. The differences between the two bacterial strains was essentially in a sensory nature.

TABLE II

| Product | Biomass inoculum (g/l) | pH before fermentation | pH after fermentation | Fermentation conditions time (h) | Temp. (°C.) | L(+) lactic acid produced L(+) lactic acid (g/l) | Proportion (%) |
|---|---|---|---|---|---|---|---|
| Apple juice, naturally cloudy | 3.0 | 3.4 | 3.4 | 72 | 33 | 7.8 | 96 |
| Apple juice | 3.0 | 3.6 | 3.4 | 72 | 33 | 7.5 | 99 |
| Grape juice, white | 6.0 | 3.4 | 3.4 | 72 | 33 | 6.8 | 96 |
| Grape juice, red | 6.0 | 3.4 | 3.2 | 72 | 33 | 7.0 | 96 |
| Orange juice | 6.0 | 3.6 | 3.2 | 72 | 20 | 7.2 | 95 |
| Peach nectar | 3.0 | 3.5 | 3.2 | 48 | 33 | 5.7 | 95 |
| Apricot nectar | 3.0 | 3.4 | 3.3 | 48 | 33 | 5.5 | 95 |

TABLE II-continued

| Product | Biomass inoculum (g/l) | pH before fermentation | pH after fermentation | Fermentation conditions time (h) | Temp. (°C.) | L(+) lactic acid produced L(+) lactic acid (g/l) | Proportion (%) |
|---|---|---|---|---|---|---|---|
| Cherry nectar | 3.0 | 3.4 | 3.3 | 48 | 33 | 9.7 | 98 |
| Black currant nectar | 6.0 | 3.3 | 3.1 | 72 | 33 | 5.2 | 96 |

TABLE III

Analytical Data for Lactic Acid Fermented Products

| | | Naturally cloudy apply juice | | Peach nectar | | Grape juice, white | |
|---|---|---|---|---|---|---|---|
| | | 0-test | ferm. test | 0-test | ferm. test | 0-test | ferm. test |
| Sugar content | °Brix | 12.0 | 11.9 | 15.1 | 15.0 | 17.0 | 16.8 |
| pH | | 3.3 | 3.4 | 3.6 | 3.4 | 3.6 | 3.6 |
| Total acid* | g/l | 7.3 | 4.6 | 3.1 | 6.0 | 7.9 | 7.1 |
| L(+) lactic acid | g/l | — | 7.0 | — | 6.1 | — | 5.7 |
| D(−) lactic acid | g/l | — | 0.1 | — | 0.3 | — | 0.1 |
| Malic acid | g/l | 7.3 | n.d. | 1.8 | n.n. | 5.0 | 0.1 |
| Citric acid | g/l | 0.2 | 0.1 | 1.8 | 1.6 | 0.4 | 0.3 |
| Glucose | g/l | 25.4 | 20.9 | 43.5 | 39.1 | 90.2 | 75.8 |
| Fructose | g/l | 64.8 | 58.3 | 43.3 | 38.8 | 89.5 | 76.9 |
| Sucrose | g/l | 22.0 | 20.0 | 44.0 | 44.0 | n.n. | n.n. |
| Biomass inoculum | g/l | — | 3.0 | — | 3.0 | — | 3.0 |
| Fermentation time | h | — | 72 | — | 48 | — | 66 |
| Fermentation temp. | °C. | — | 33 | — | 33 | — | 33 | n.d. = not detectable
*calculated as tartaric acid for apple juice, as citric acid for peach nectar, as tartaric acid for grape juice The table shows that for all the fruit juice products enumerated above, the required characteristics, namely at least 95% L(+) lactic acid referred to the total lactic acid, is attainable in absolute amounts of L(+) lactic acid of at least 5 g/liter during fermentation below pH 3.7. The other process conditions are to be adapted to the special initial products within the limits claimed. As apparent from the table, certain juices require a greater amount of biomass incculum and about 50% longer fermentation time.

Table III, herein below, gives details for three products about the changes in the acid and sugar levels occurring during fermentation.

The present invention is further illustrated by reference to the drawings, wherein:

FIG. 3 is a graph of lactic acid formation as a function of fermentation time for apricot nectar.

Figure 1:
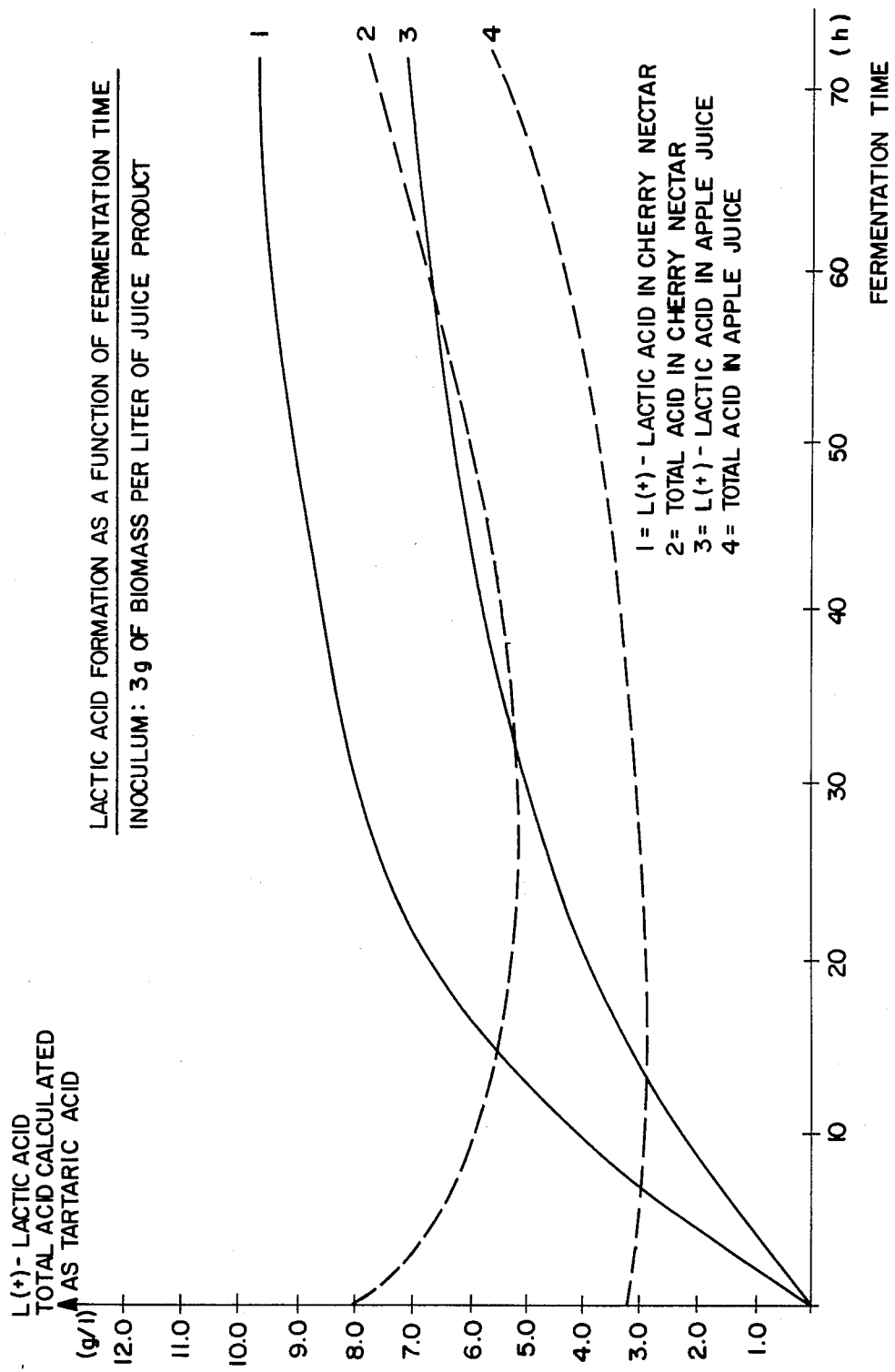
FIG. 1 is a graph of lactic acid formation as a function of fermentation time for cherry nectar and apple juice.

Described in further detail, FIG. 1 shows the content of L(+) lactic acid and the total acid, calculated as tartaric acid, as a function of the fermentation time for cherry nectar and apple juice for an inoculum of 3 g of biomass per liter of juice product. Accordingly, the required L(+) lactic acid content for apple juice is attained only after a fermentation time of about 30 hours, whereas this occurs as early as approximately 13 hours for cherry nectar. The graph also shows that very long fermentation times produce no additional major increase in L(+) lactic acid.

Figure 2:
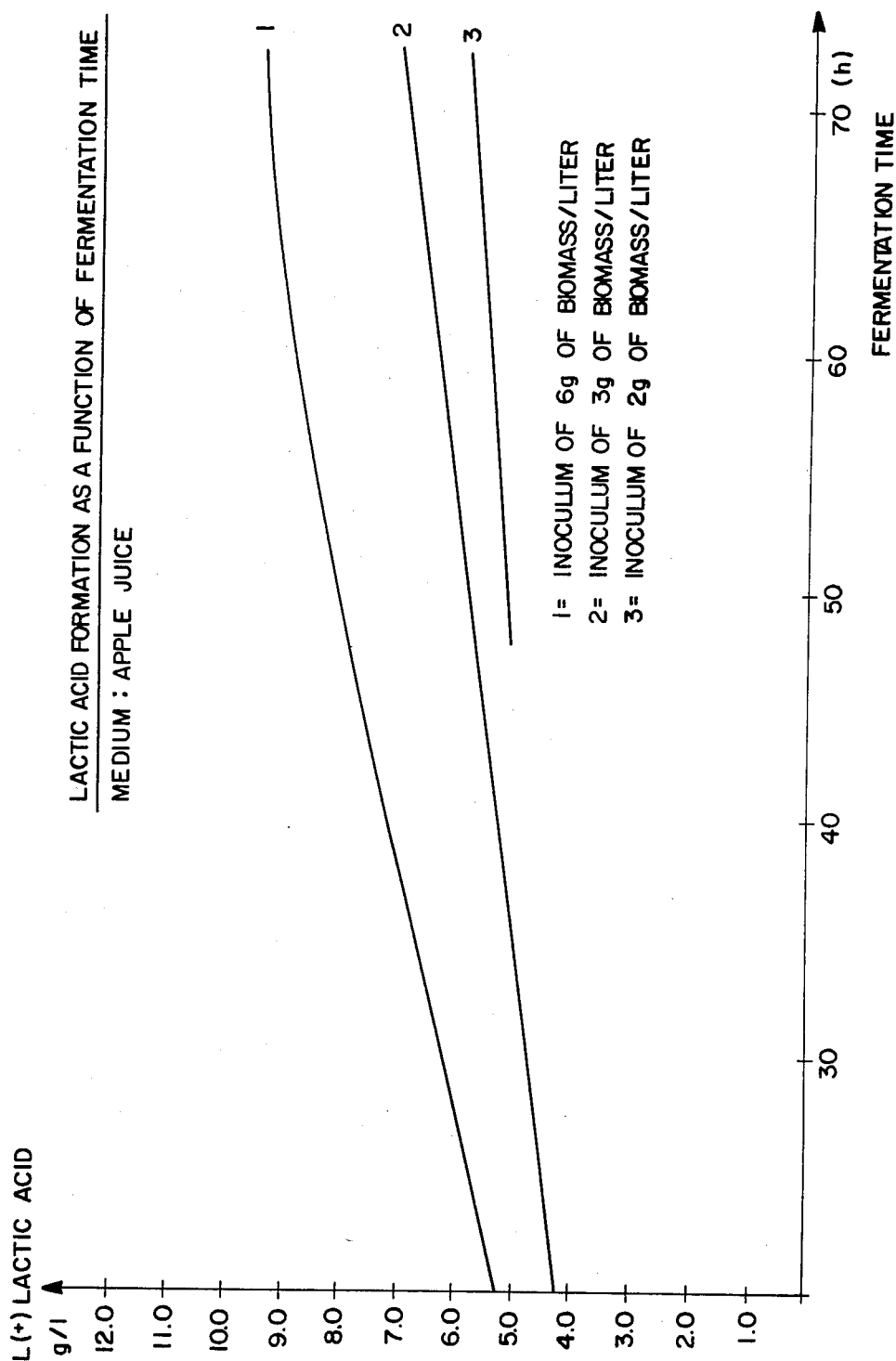
FIG. 2 is a graph of lactic acid formation as a function of fermentation time for apple juice.

FIGS. 2 and 3 show the attainable L(+) lactic acid content first for apple juice, then for apricot nectar for different amounts of biomass inoculum.

The following examples serve to illustrate the present invention.

EXAMPLE 1

Lactic Acid Fermentation of Naturally Cloudy Apple Juice (a) Culturing of biomass The lyophilized bacterial culture is suspended in physiologic saline and is transferred to 50 ml of MRS broth. After 24 hours at 33° C., the entire first culture is incubated in 500 ml of MRS broth for 24 hours at 33° C. This produces about 7.5 g of biomass. The biomass thus obtained is harvested under sterile conditions and used as the fermentor culture. BETA nutrient solution is introduced aseptically into the fermentor. For inoculation, 1 g of the biomass from the second culturing per liter of broth is used. A biomass yield of about 55 g/liter is obtained by the concurrent addition of a pH-regulating solution and a glucose solution of a specific concentration.

After culturing is completed (24 hours at 33° C.), the fermentation solution is placed in a sterile container, and the biomass is collected from the spent nutrient solution under sterile conditions by a membrane separation procedure. The lactobacilli are purified in physiologic saline and again separated. The biomass is a white, highly viscous mass and constitutes a pure culture. Membrane separation procedures are known in the art and any suitable method may be used.

(b) Procedure for carrying out the fermentation

Naturally cloudy apple juice with a pH of 3.4 is introduced in the amount of 100 ml into a sterile tank via a plate heat exchanger (HKZE 90° C.), HKZE=high short time heating. Inoculation is performed with 3 g of the biomass obtained in (a) above containing 3 g/l juice. If large containers are used, the juice must be stirred slowly. After 72 hours of fermentation time at 33° C., about 7.5 g of L(+) lactic acid per liter is produced. The lactic acid of the juice product thus obtained consists of about 99 weight % L(+) lactic acid and 1% D(−) lactic acid. The lactic acid fermented, naturally cloudy apple juice is adjusted to 5 g of L(+) lactic acid per liter of end product with 50 l of unfermented initial product and is packaged commercially by hot bottling. Such bottling procedures are known in the art. The fermentation was also carried out using the different bacterial strains *Lactobacillus casei, subspecies casei* (Beta 3 strain), and Lactobacillus sp. (Beta 8 strain). The resulting properties obtained exhibited only distinctions of a sensory nature.

EXAMPLE 2

Lactic Acid Fermentation of Grape Juice

Red or white grape juice in the amount of 10 l and a pH of 3.4 is introduced into a sterile tank via a plate heat exchanger (HKZE 85° C.) and is inoculated with 6 g of biomass of the strain Beta 8 per liter of juice. Culturing of bacteria is performed as described in Example 1 (a) above. After 72 hours at 33° C., 7.0 g/liter of L(+) lactic acid is produced; the proportion of this nutritionally and physiologically important L(+) lactic acid is 96%. After the fermentation the lactobacilli are separated by means of a separator. If this processing step is used, the bacteria can be reused. The fermented product is then adjusted with 4 l of fresh juice to 5.0 g/liter of L(+) lactic acid, filtered, stabilized with potassium bitartrate, and subsequently bottled at 85° C. according to HKZE.

EXAMPLE 3

Lactic Acid Fermentation of Peach Nectar

Peach nectar, in the amount of 10 l are produced from peach pulp and sugar water in a volume ratio of 1:1, with a sugar content of 15° Brix is then introduced aseptically into the fermentation tank via a plate heat exchanger (HKZE 110° C.). Inoculation is performed with 30 g of the biomass (strain Beta 8) obtained as in Example 1 (a). After 48 hours at 33° C., the pH drops from 3.6 to 3.4. The L(+) lactic acid concentration is 6.0 g/liter. The lactic acid consists of up to 95% L(+) lactic acid and up to 5% D(−) lactic acid.

The fermented product is blended with 2.5 l unfermented initial product to 5 g/liter of L(+) lactic acid and bottled according to HKZE (110° C.).

EXAMPLE 4

Preparation of Lactic Acid Fermented Cherry Preserves

Cherry pulp in the amount of 10 l and 15° Brix with a pH of 3.4 is subjected to a lactic acid fermentation, wherein the pulp is briefly pasturized at 85° C. (HKZE 85°) and then introduced into a sterile tank. There is then added to the pulp 6 g/l of a biomass of the bacterial strain Beta 3. After 72 hours fermentation time at 33° C., there is obtained 11 g/l of L(+) lactic acid. The proportion of L(+) lactic acid was 98% of the total lactic acid produced in this way.

The fermented pulp was concentrated 3 fold in a thin film evaporator and, with the addition of sugar and binder, mixed, sterilized and brought to the form of a ready to sell cherry preserve.

When used for the manufacture of jams, fruit base, jellies, spreads and the like which are based on the use of fruit pulp products, the lactic acid product of the invention is mixed with conventional ingredients according to known receipes and procedures.

It is within the scope of the present invention to provide a process for the production of fruit pulp and fruit juice products that have a pH of less than 3.7, preferably less than 3.5, and a malic acid content of less than 1 g/l, preferably less than 0.2 g/l. Included among such fruit products are fruit preserves, jellies, spreads and jams.

Further variations and modifications of the invention will be apparent to those skilled in the art from the foregoing and are intended to be encompassed by the claims appended hereto.

The German priority application No. P 35 03 742.3 is incorporated and relied on herein.

We claim:

1. A process for the preparation of lactic acid fruit products comprising providing an initial product in the form of a fruit mash or fruit juice at a pH of less than 3.7, heat treating said initial product at a temperature and for a period of time sufficient to destroy wild microflora contained therein and subjecting said heat treated initial product to fermentation at a pH of less than 3.7 by lactic acid producing bacteria, said fermentation being carried out at a sufficient temperature and for a sufficient period of time to thereby produce a product containing at least 95% by weight of L(+) lactic acid as the fermentation product, wherein said bacteria are those whose lactic acid producing metabolic pathways are induced and which commence and continue L(+) lactic acid production at pH values below 3.7.

2. The process as set forth in claim 1, wherein the fermentation is carried out for a sufficient period of time to form at least 5 g of the L(+) lactic acid per liter of fermentation product.

3. The process as set forth in claim 1, wherein the fermentation is carried out by adding biomass in the form of a pure culture of the lactic acid producing bacteria to the initial product.

4. The process as set forth in claim 3, wherein said pure culture biomass is added in an amount of at least 1 g of biomass per liter of the initial product.

5. The process as set forth in claim 4, wherein 2 to 10 g of biomass is added to the initial product per liter of the initial product.

6. The process as set forth in claim 5, wherein 2 to 6 g of biomass is added to the initial product per liter of the initial product.

7. The process as set forth in claim 1, wherein the fermentation time is at least 24 hours.

8. The process as set forth in claim 7, wherein the fermentation time is up to 100 hours.

9. The process as set forth in claim 1, wherein the fermentation is carried out at temperatures between 15° and 40° C.

10. The process as set forth in claim 9, wherein the fermentation is carried out at temperatures between 25° C. and 35° C.

11. The process as set forth in claim 3, wherein said biomass is grown in the presence of a nutrient growth solution, is thereafter separated from the nutrient growth solution, and then purified.

12. The process as set forth in claim 1, wherein Lactobacillus sp. corresponding to deposit No. DSM 3174 is used.

13. The process as set forth in claim 1, wherein *Lactobacillus casei subspecies casei*, is used for the fermentation.

14. The process as set forth in claim 13, wherein *Lactobacillus casei subspecies casei* corresponding to deposit No. DSM 3173 is used.

15. The process as set forth in claim 1, wherein the fermentation is carried out at a pH of less than 3.7 for a substantial portion of the process.

16. A process for the production of a fruit pulp or fruit juice containing product comprising adding to said fruit pulp or said fruit juice which has a pH of less than 3.7 an effective amount of the L(+) lactic acid product produced by the process of claim 1 to thereby obtain a product having at least 5 g/l of L(+) lactic acid.

17. The process as set forth in claim 1 which further comprises formulating the fruit mash into a fruit preserve, jelly, spread or jam.

* * * * *